United States Patent

Kettlitz et al.

[11] Patent Number: 6,090,594
[45] Date of Patent: Jul. 18, 2000

[54] PROCESS FOR PREPARING STARCHY PRODUCTS

[75] Inventors: Bernd Wolfgang Kettlitz, Grimbergen, Belgium; Edwin Theodoor Petrus Bertine Maria Moorthamer, Hulst, Netherlands; Horst Anger, Stahnsdorf; Gisela Renate Stoof, Ludwigsfelde, both of Germany

[73] Assignee: Cerestar Holding B.V., Sas Van Gent, Germany

[21] Appl. No.: 08/826,808

[22] Filed: Mar. 25, 1997

Related U.S. Application Data

[63] Continuation of application No. 08/422,525, Apr. 14, 1995, abandoned.

[30] Foreign Application Priority Data

Apr. 15, 1994 [GB] United Kingdom .................... 0407514
Oct. 1, 1994 [GB] United Kingdom .................... 9419812

[51] Int. Cl.⁷ ............................. C12P 19/16; C12P 19/04; C08B 30/00; A23L 1/0522
[52] U.S. Cl. ............................. 435/98; 435/99; 435/101; 536/102; 426/661
[58] Field of Search ................................. 435/98, 99, 101; 426/661; 536/102

[56] References Cited

U.S. PATENT DOCUMENTS

| | | | |
|---|---|---|---|
| 3,766,011 | 10/1973 | Kurimoto et al. | 435/98 |
| 3,788,946 | 1/1974 | Kurimoto et al. | 435/98 |
| 3,881,991 | 5/1975 | Kurimoto et al. | 435/98 |
| 4,971,723 | 11/1990 | Chiu | 252/315.3 |
| 5,281,276 | 1/1994 | Chiu et al. | 127/65 |
| 5,409,542 | 4/1995 | Henley et al. | 127/65 |

FOREIGN PATENT DOCUMENTS

| | | | |
|---|---|---|---|
| 564893 | 10/1993 | European Pat. Off. | |
| WO-A-9015147 | 12/1990 | WIPO | |

*Primary Examiner*—Francisco Prats
*Attorney, Agent, or Firm*—Pillsbury Madison & Sutro LLP

[57] ABSTRACT

The invention relates to a starch composition containing a relatively high proportion of so called "resistant starch" structures. The compositions of the invention are obtained by debranching an aqueous slurry of a gelatinized starch and retrograding the resulting product

17 Claims, No Drawings

PROCESS FOR PREPARING STARCHY PRODUCTS

This is a continuation of application Ser. No. 08/422,525, filed on Apr. 14, 1995, which was abandoned upon the filing hereof.

BACKGROUND OF THE INVENTION

1. Field of the Invention

The present invention relates to a starch composition containing a relatively high proportion of so-called "resistant starch" structures.

2. Background Information

It has been known for many years that starches, which commonly consist of varying proportions of amylose and amylopectin, may be subjected to an enzymatic treatment which reduces the content of the highly branched amylopectin and increases the content of short-chain amylose structures (see, for example, U.S. Pat. No. 3,729,380). It is also known that the products of such enzymatic treatment are more prone to retrogradation than normal starches and produce in this manner compositions containing increased amounts of resistant starch structures. Resistant starch (RS) is resistant to attack by alpha-amylase and may be used therefore as a low calorie bulking component in food compositions so contributing to the dietary fibre content of such compositions.

The treatment of the starch with the debranching enzyme takes place in an aqueous slurry which, for handling reasons, cannot be too concentrated. It would clearly be attractive therefore to be able to use a starchy composition at a higher concentration than normal while at the same time increasing the amount of RS formed as a proportion of the starchy material treated. EP 564 893 A describes and claims a process for the production of a RS product containing at least about 15% RS in which an aqueous slurry of starch containing at least 40% amylose is gelatinised and debranched by treatment with a debranching enzyme which hydrolyses 1,6-glucosidic bonds in the starch molecules, the debranched product subsequently being retrograded to produce RS. The optimum starch concentration in the aqueous slurry is said to be about 15% and the Examples of 564 893 A illustrate the process by using starch slurries containing 14% to 17% starch respectively. The starch starting material contains at least 40% amylose and for a corn (maize) starch containing 25% amylose it is shown that no RS is formed in the process. As the percentage of amylose in the starch starting material increases above 40% so does the RS in the product of the process until a starch containing 100% amylose is shown to produce a product containing 50.3% RS.

SUMMARY OF THE INVENTION

We have now found a method of producing a starchy composition containing a relatively large amount of RS structures from a starting material which contains less than 40% amylose and which can be debranched in slurries containing more than 15% solids.

Accordingly, the invention is a process for the production of a product containing RS structures in which an aqueous slurry of a gelatinised starch is debranched by a debranching enzyme and the resulting product retrograded and which is characterised in that the aqueous slurry contains at least 20% by weight solids and is a slurry of a partially degraded, root or tuber starch.

Preferably the product of the process comprises at least about 25% by weight RS, more preferably 30% by weight or more RS, particularly over 50% by weight RS.

By "partially degraded starch" is meant starch which has been treated to reduce the amylose/amylopectin chain length and hence the average molecular weight of the starch in question. The degradation treatment is conducted by known means and includes hydrolysis, either acid or enzyme catalysed, extrusion, oxidation or pyrolysis. One preferred partially degraded root or tuber starch is the so called "acid thinned" starch, particularly acid thinned potato starch, in which the potato starch granules are treated with acid in water suspension at sub-gelatinising temperature whereby the starch granules remain superficially unchanged. A second preferred partially degraded root or tuber starch is a maltodextrin, more preferably a potato starch maltodextrin which suitably has a DE (dextrose equivalent) of 1 to 19 preferably 2 to 10 more preferably 2 to 5. Such potato starch maltodextrins are produced from potato starch containing about 25% amylose. Other root or tuber starch maltodextrins which may be used in the process include tapioca maltodextrins.

The aqueous slurry of the maltodextrin used in the process according to the invention contains at least 20% by weight solids but may be more concentrated and may contain 30% by weight or more solids.

The debranching enzymes which may be used in the process are those known for this purpose ie pullulanases and isoamylases or mixtures thereof. Depending upon the nature of the specific enzyme chosen, the debranching may be carried out at a temperature in the range 25° to 75° C., preferably 50° to 60° C., and at a pH in the range 3 to 7.5, preferably in the range 5 to 6. The treatment generally lasts up to 24 hours and at its conclusion the enzyme is deactivated by lowering the pH to 3 or less and/or by increasing the temperature to above that tolerated by the enzyme in question.

On completion of the enzymatic treatment the retrogradation of the amylose structures is effected by allowing the aqueous reaction product to stand, suitably at a temperature in the range 0 to 30° C. and for a period of up to three days, more preferably for a period of 1 to 36 hours. Following the completion of the retrogradation the composition is dried, eg. by spray drying, to give a powdered product containing up to 60% by weight RS particularly 25 to 55% by weight RS which is suitable for use as a component of various food compositions.

DETAILED DESCRIPTION OF THE INVENTION

The invention will now be further described by reference to the following Examples in which the determinations of RS were made by the following method.

A 5% by weight suspension in water of the retrograded starch product is thoroughly homogenised in an acetate buffer solution. The acetate buffer is made by dissolving 8.2 g anhydrous sodium acetate in 250 ml of an saturated aqueous solution of benzoic acid, adding 4 ml of 1M calcium chloride and making up to 800 ml with distilled water before adjusting the pH to 5.2 with acetic acid and finally making up to 1000 ml with distilled water. 25 ml of the suspension are incubated with 1 ml pancreatic solution for 24 hours at 37° C. in a shaking water bath. The incubated suspension is next stirred into 119 ml of 95% alcohol, filtered and the filtration residue dried and its starch content determined acording to the relationship:

$$RS = \frac{\text{starch content of the residue (on a dry basis)} \times 100}{\substack{\text{starch content of the suspension} \\ \text{before incubation (on a dry basis)}}}$$

The pancreatic solution is made by stirring 2 g pancreatin with 12 ml distilled water for 10 minutes, centrifuging and using the supernatant liquid as the pancreatic solution.

EXAMPLE 1

25 kg potato starch maltodextrin with a dextrose equivalent of about 3 was dissolved in water to give a concentration of 25% by weight. The suspension was heated to 50° C. and the pH adjusted to 5.0. After adding 25 ml isoamylase (product EN102 of Hayashibara Biochemical Laboratories Inc), the reaction was allowed to proceed for 20 hours after which time the temperature was increased to 80° C. and the pH reduced to 3.0 for 1 hour in order to deactivate the enzyme. The average Mol. wt. after debranching was 13680 as determined by GPC. The amount of oligomers with $DP \leq 10$ was 22%.

After readjustment of the pH to 5.0 the suspension was cooled to 4° C. and held at this temperature for 24 hours. The weak gel that formed was easily destroyed by stirring and the suspension finally brought to 15% by weight by dilution with water and spray dried. This product contained 28.9% RS compared with the maltodextrin before debranching which formed only 7.3% RS under comparable retrogradation conditions.

EXAMPLE 2

This example demonstrates the influence of the retrogradation conditions on the formation of resistant starch. The debranched maltodextrin used was essentially the same as that described in Example 1.

For 24 hours retrogradation the following conditions were compared:

concentration: 10%, 30% by weight
temperature: 4° C.; 25° C.

The following amounts of RS (% by weight) were detected

|  | 10% | 30% |
|---|---|---|
| 4° C. | 31.8 | 28.5 |
| 25° C. | 27.2 | 26.4 |

This Example shows that retrogradation at 25° C. gives only a slightly lower figure for resistant starch compared with retrogradation at 4° C. The lower concentration of debranched starch (10% by weight) in the slurry leads to the formation of a slightly increased amount of resistant starch compared with the slurry containing 30% by weight debranched starch.

EXAMPLES 3 to 5

In Examples 3 to 5 the process used was the same as that described in Example 1 replacing the potato starch maltodextrin by other starting materials within the scope of the present invention. These starting materials and the experimental results obtained are given in the following table

| Example | Starting material | M. wt (Mw) before debrancing | M. wt (Mw) after debranching | Oligomers $DP \leq 10$ | R.S. % before debranching | R.S. % after debranching |
|---|---|---|---|---|---|---|
| 3 | Acid thinned potato starch | 52,180 | 9340 | 4.5% | 20.0 | 51.8 |
| 4 | Potato starch pyrodextrin | 106,500 | 11,530 | 5.8% | 4.9 | 28.0 |
| 5 | Tapioca starch maltodextrin (DE approx 2) | 129,600 | 19,770 | 13% | 2.4 | 25.6 |

EXAMPLE 6

A regular corn starch maltodextrin with a dextrose equivalent of 3 was treated in the same way as that described for potato maltodextrin in Example 1.

After debranching the product had a average Mol. Wt. of 14390 as determined by GPC and contained 20% oligosaccharides with $DP \geq 10$. The product was retrograded at respectively 4° C. and 25° C. for 24 hours. The following amounts of resistant starch were determined:

4° C.=10.0%

25° C.=8.3%

This example shows that a debranched corn maltodextrin forms much less RS than a debranched potato maltodextrin under the same conditions of treatment. Because the amylose contents of corn starch and potato starch differ only marginally the amylose content cannot be the reason for the large difference in resistant starch. It seems probable therefore that debranching of the partially hydrolysed potato amylopectin liberates more linear fragments which are capable of being retrograded to resistant structures.

EXAMPLE 7

A waxy maize starch maltodextrin with a DE of about 4 was treated by the process described in Example 1. The debranched product was found to have a Mw of 12010 but after holding at 4° C. for 24 hours the amount of resistant starch (RS) which was formed amounted to only 0.3%.

What is claimed is:

1. A process for the production of a product containing resistant starch (RS) structures, said product comprising at least about 25% by weight resistant starch, said process comprising fully debranching an aqueous slurry of a gelatinised starch by means of a debranching enzyme and retrograding the resulting product, wherein the aqueous slurry comprises at least 20% by weight solids and is a slurry of a partially degraded root or tuber starch, which is an acid-thinned starch or a maltodextrin having a DE of 2 to 10, said starch containing less than 40% amylose.

2. A process according to claim 1 wherein the product comprises at least about 30% by weight resistant starch.

3. A process according to claim 1 wherein the product comprises at least about 50% by weight resistant starch.

4. A process according to claim 1 wherein the aqueous slurry comprises at least 30% by weight solids.

5. A process according to claim 1 wherein the debranching enzyme is a pullulanase or isoamylase or a mixture thereof, the debranching process is carried out at a temperature in the range 25° to 75° C. and at a pH in the range 3 to 7.5.

6. A process according to claim 1 wherein the retrogradation is carried out by allowing the aqueous debranched starch product to stand.

7. A process according to claim 1 wherein the acid thinned starch is acid thinned potato starch and the maltodextrin is a potato starch maltodextrin.

8. A process according to claim 1 wherein the maltodextrin has a DE of 2 to 5.

9. A process according to claim 7 wherein the maltodextrin has a DE of 2 to 5.

10. A process according to claim 8 wherein the aqueous slurry comprises at least 30% by weight solids.

11. A process according to claim 10 wherein the debranching enzyme is a pullulanase or isoamylase or a mixture thereof, the debranching process is carried out at a temperature in the range 25° to 75° C. and at a pH in the range 3 to 7.5.

12. A process according to claim 1 wherein the retrogradation is carried out by allowing the aqueous debranched starch product to stand.

13. A process according to claim 12 wherein the product is allowed to stand at a temperature in the range 0° to 30° C. for a time period in the range of 1 to 36 hours.

14. A process according to claim 13 wherein the product after retrogradation is spray dried to give a powdered product containing up to 60% by weight RS.

15. A process according to claim 14 wherein the product after retrogradation is spray dried to give a powdered product containing 25 to 55% by weight RS.

16. A process according to claim 1 wherein the root or tuber starch is a potato starch or tapioca.

17. A food composition comprising an RS product made by the process of one of claims 1–15.

* * * * *